(12) United States Patent  
Christenson (10) Patent No.: US 9,259,530 B2  
(45) Date of Patent: Feb. 16, 2016

(54) IMPLANTABLE INFUSION DEVICE

(75) Inventor: Steven R. Christenson, Coon Rapids, MN (US)

(73) Assignee: Medtronic, Inc., Minneapolis, MN (US)

( * ) Notice: Subject to any disclaimer, the term of this patent is extended or adjusted under 35 U.S.C. 154(b) by 1136 days.

(21) Appl. No.: 12/625,694

(22) Filed: Nov. 25, 2009

(65) Prior Publication Data

US 2011/0125137 A1      May 26, 2011

(51) Int. Cl.
| | | |
|---|---|---|
| *A61M 5/142* | (2006.01) | |
| *A61M 5/14* | (2006.01) | |
| *A61M 5/168* | (2006.01) | |
| A61M 39/24 | (2006.01) | |
| A61M 39/02 | (2006.01) | |

(52) U.S. Cl.
CPC ....... *A61M 5/14276* (2013.01); *A61M 5/16813* (2013.01); *A61M 5/141* (2013.01); *A61M 2039/0244* (2013.01); *A61M 2039/242* (2013.01)

(58) Field of Classification Search
CPC .............. A61M 2005/14513; A61M 5/16827; A61M 5/168; A61M 5/16804; A61M 5/16813; A61M 5/16877; A61M 5/16881; A61M 5/141; A61M 2039/242
USPC ........... 604/891.1, 890.1; 605/288.01–288.04
See application file for complete search history.

(56) References Cited

U.S. PATENT DOCUMENTS

| | | | |
|---|---|---|---|
| 4,193,397 A | | 3/1980 | Tucker |
| 4,258,711 A | * | 3/1981 | Tucker et al. ................. 604/502 |
| 4,714,462 A | * | 12/1987 | DiDomenico .................. 604/67 |
| 5,049,141 A | | 9/1991 | Olive |
| 6,048,328 A | * | 4/2000 | Haller et al. ............. 604/288.03 |
| 6,471,675 B1 | * | 10/2002 | Rogers et al. ................. 604/151 |
| 6,488,652 B1 | * | 12/2002 | Weijand et al. ............ 604/93.01 |
| 6,554,822 B1 | | 4/2003 | Holschneider |
| 6,635,049 B1 | | 10/2003 | Robinson |
| 6,979,315 B2 | | 12/2005 | Rogers |
| 2004/0059315 A1 | | 3/2004 | Erickson |

FOREIGN PATENT DOCUMENTS

WO    WO 2007/093778      8/2007

* cited by examiner

*Primary Examiner* — Nicholas Lucchesi  
*Assistant Examiner* — Weng Lee  
(74) *Attorney, Agent, or Firm* — Mueting, Raasch & Gebhardt, P.A.

(57) ABSTRACT

An implantable infusion device includes a positive pressure reservoir, a pump, a flow restrictor, and an outlet. The device includes a first fluid flow path from the reservoir to the outlet, where the pump is downstream of the reservoir, and the outlet is downstream of the pump. The device further includes a second fluid flow path from the reservoir to the outlet, where the flow restrictor is downstream of the reservoir, and the outlet is downstream of the restrictor. The device may also include one or more controllable, MRI-safe valves to select whether fluid is delivered via the first or second flow path.

6 Claims, 7 Drawing Sheets

IMPLANTABLE INFUSION DEVICE

FIELD

This disclosure relates to infusion devices, particularly implantable infusion devices having two flow paths capable of delivering fluid at different rates.

BACKGROUND

A wide variety of implantable infusion devices are available for delivering fluid to target locations of patients into which the devices are implanted. Available and proposed devices can differ in their ability to control the flow rate of fluid delivered from the device to the patient. For example, Medtronic Inc.'s (Minneapolis, Minn.) SYNCHROMED series of implantable infusion devices are programmable devices where the flow rate may be varied according to instructions provided by, e.g., a physician programmer device. Programmable implantable infusion devices can provide a wide range of fluid flow rates and are typically designed to deliver small amounts of therapeutic agent over time.

Such devices have been used successfully to treat a variety of diseases. However, in some patients it may be desirable to deliver a bolus infusion of therapeutic agent that exceeds the amount deliverable by existing programmable infusion devices. For example, it may be desirable to deliver 1 milliliter or more in a minute. While devices that can accomplish such infusion rates are theoretically possible, such devices may suffer certain safety drawbacks, such as MRI safety.

When a patient having an implanted infusion device is subjected to an MRI procedure, the magnetic field may result in unpredictable opening or closing of valves in the infusion device. If a device capable of delivering a high infusion rate requires a valve to control the delivery of therapeutic agent, unpredictable opening of the valve during an MRI procedure may result in an undesired or unsafe amount of therapeutic agent to be delivered to the patient during the MRI procedure.

BRIEF SUMMARY

The present disclosure describes, among other things, implantable infusion devices that are MRI-safe, have the advantages of programmable pumps, and are capable of delivering high rates of therapeutic agent. In many embodiments described herein, the implantable infusion devices include two flow paths. The first flow path includes a programmable pump mechanism to provide for a variable flow rate. The second flow path allows for delivery of fluid at a bolus rate that is higher than the flow rate achievable via the first flow path. Valves that are stable when subjected to magnetic fields may be employed to select whether fluid exits the device via the first or second fluid paths and to provide MRI safety.

In various embodiments, this disclosure describes an implantable infusion device including a positive pressure reservoir, a pump, an active valve, a safety valve, a flow restrictor, and an outlet. The device includes a first fluid flow path from the reservoir to the outlet, where the pump is downstream of the reservoir, the first active valve is downstream of the pump, and the outlet is downstream of the first active valve. The device further includes a second fluid flow path from the reservoir to the outlet, where the safety valve is downstream of the reservoir, the flow restrictor is downstream of the safety valve, and the outlet is downstream of the reservoir. The device also includes a third fluid flow path from the pump to the safety valve. The safety valve is configured to prevent flow from the reservoir to the outlet via the second flow path unless the first active valve is closed and the pump is activated. The first flow path provides a flow path of a programmable pump, while the second flow path provides for delivery of fluids at high flow rates. The safety valve prevents unintended delivery of fluids via the second flow path, making the device MRI-safe.

In some embodiments, an implantable infusion device described herein includes a positive pressure reservoir, a pump, a flow restrictor and one or more MRI-safe active valves. The device includes a first fluid flow path from the reservoir to the outlet, where the pump is downstream of the reservoir and the outlet is downstream of the pump. The device further includes a second fluid flow path from the reservoir to the outlet, where the flow restrictor is downstream of the reservoir, and the outlet is downstream of the restrictor. One or more active MRI-safe valves, such as piezoelectric valves, may be employed upstream or downstream of the restrictor or pump to control whether fluid exits the outlet via the first or second flow path.

Advantages of the devices and methods described herein will be evident to one of skill in the art upon reading the disclosure herein.

The drawings are not necessarily to scale. Like numbers used in the figures refer to like components, steps and the like. However, it will be understood that the use of a number to refer to a component in a given figure is not intended to limit the component in another figure labeled with the same number. In addition, the use of different numbers to refer to components is not intended to indicate that the different numbered components cannot be the same or similar.

DETAILED DESCRIPTION

In the following detailed description, reference is made to the accompanying drawings that form a part hereof, and in which are shown by way of illustration several specific embodiments of devices, systems and methods. It is to be understood that other embodiments are contemplated and may be made without departing from the scope or spirit of the present disclosure. The following detailed description, therefore, is not to be taken in a limiting sense.

All scientific and technical terms used herein have meanings commonly used in the art unless otherwise specified. The definitions provided herein are to facilitate understanding of certain terms used frequently herein and are not meant to limit the scope of the present disclosure.

As used in this specification and the appended claims, the singular forms "a", "an", and "the" encompass embodiments having plural referents, unless the content clearly dictates otherwise.

As used in this specification and the appended claims, the term "or" is generally employed in its sense including "and/or" unless the content clearly dictates otherwise.

The present disclosure describes, among other things, implantable infusion devices having advantages of programmable pumps and that are capable of delivering high rates of therapeutic agent. The devices have alternative flow paths that provide for lower or higher flow rates. The devices employ a positive pressure reservoir, and in many embodiments, employ a pump to control fluid flow via a lower flow rate pathway and employ a flow restrictor to deliver fluid via a higher flow rate pathway. The devices may be configured to prevent inadvertent fluid delivery when subjected to a magnetic field, such as experienced during an MRI procedure, by employing valves that are stable when subjected to a magnetic field.

Figure 1:
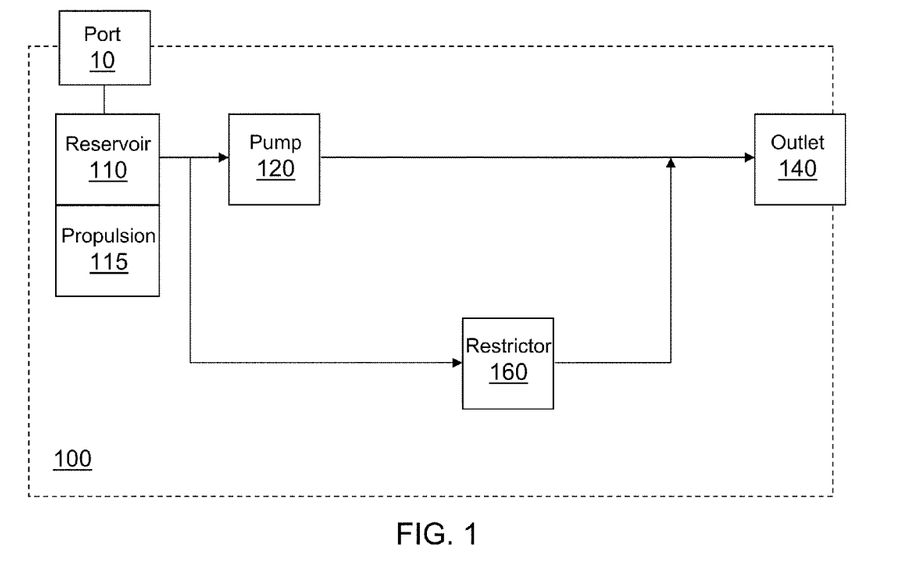
FIGS. 1-4 are schematic block diagrams showing some components of embodiments of implantable infusion devices.

Referring now to FIG. 1, an implantable infusion device 100 having two fluid flow pathways is shown. The device has a hermetically sealed housing in which some or all of the components are stored. The device 100 also includes a reservoir 110 for storing fluid, which typically is a liquid composition including a therapeutic agent, and an outlet 140 through which the fluid can be delivered. The two flow paths extend from the reservoir 110 to the outlet 140. For purposes of the present disclosure, the reservoir 110 is discussed as being "upstream" of the outlet 140 in the flow path. The first flow path includes a pump 120 downstream of the reservoir 110 and upstream of the outlet 140. Any suitable active pump may be employed, such as a piston pump, a peristaltic pump, a diaphragm pump, or the like. The pump 120 is configured to control the rate at which fluid from the reservoir 110 is delivered from the device 100 via the outlet 140.

Still referring to FIG. 1, the second flow path from the reservoir 110 to the outlet 140 includes a flow restrictor 160 downstream of the reservoir 110 and upstream of the outlet 140. Any suitable flow restrictor 160 may be used in the device 100. For example, a flow restrictor 160 may be a fluid conduit of restricted diametric dimension or a media to resist fluid flow. In some embodiments, the flow restrictor 160 is a capillary tube. In some embodiments, the flow restrictor 160 includes a fluidic path micro-machined in glass or silicon. In various embodiments, the flow restrictor 160 is an actuatable valve assembly. For example, the valve may resemble a needle valve in a carburetor jet where a tapered needle is advanced into or withdrawn from a tapered opening to control flow. A ball valve or any other suitable valve may also be employed.

The second flow path may typically be used to deliver fluid from the reservoir 110 at a higher flow rate than via the first flow path. The flow rate achievable by the second flow path is determined mainly by the amount of pressure in the reservoir 110 and the design of the flow restrictor 160. Depending on the design of the reservoir 110 and the pressure or force with which fluid may be expelled from the reservoir 110, the flow restrictor 160 can be configured to allow any suitable rate of fluid delivery, such as 1 milliliter or more a minute. In various embodiments, the second flow path is configured to provide a bolus flow rate of greater than 50 microliters per minute, greater than 250 microliters per minute, or greater than 500 microliters per minute.

The reservoir 110 is a positive pressure reservoir, which means the pressure in the reservoir is greater than atmospheric pressure, forcing out the fluid contents of the reservoir. As depicted in FIG. 1 and various other figures presented herein, a propulsion mechanism 115 may be operably coupled to the reservoir 110 to drive fluid out of the reservoir 110. Any suitable propulsion mechanism 115 may be employed. By way of example, the reservoir 110 may be a bellows reservoir and the propulsion mechanism 115 may contain a propellant chamber that contains a fluid whose vapor pressure is such that, under conditions of normal body temperature, pressure is exerted on the bellows to force liquid in the reservoir 110 to enter the pump 120 or the restrictor 160. Examples of such propulsion mechanisms are found in Medtronic Inc.'s SYNCHROMED and ISOMED implantable infusion devices. A mechanical spring may be readily substituted for the liquid propellant. Alternatively, reservoir 110 may be formed, at least in part, of an elastomeric or resilient material biased in an empty configuration that expands when filled and forces fluid to exit reservoir 110 and enter the pump 120 or the restrictor 160. Thus, the propulsion mechanism 115 and reservoir 110 may, in some embodiments, be the same component.

As shown in FIG. 1 and various other figures presented herein, the infusion device 100 may include a refill port 10. The refill port 10 is in fluid communication with the reservoir 110 and provides access to the reservoir 110 to allow liquid to be delivered to, or withdrawn from, the reservoir 110. The refill port 10 may include a one-way valve mechanism (not shown) that allows fluid to be delivered to the reservoir 110 but prevents fluid from escaping the reservoir 110 via the access port 10. The refill port 10 may include check valve (not shown) or other mechanism to prevent overfilling of reservoir. One or more sensors (not shown) may be employed to detect needle entry into port 10, provide feedback regarding fill status of the reservoir 110, or the like.

Figure 2:
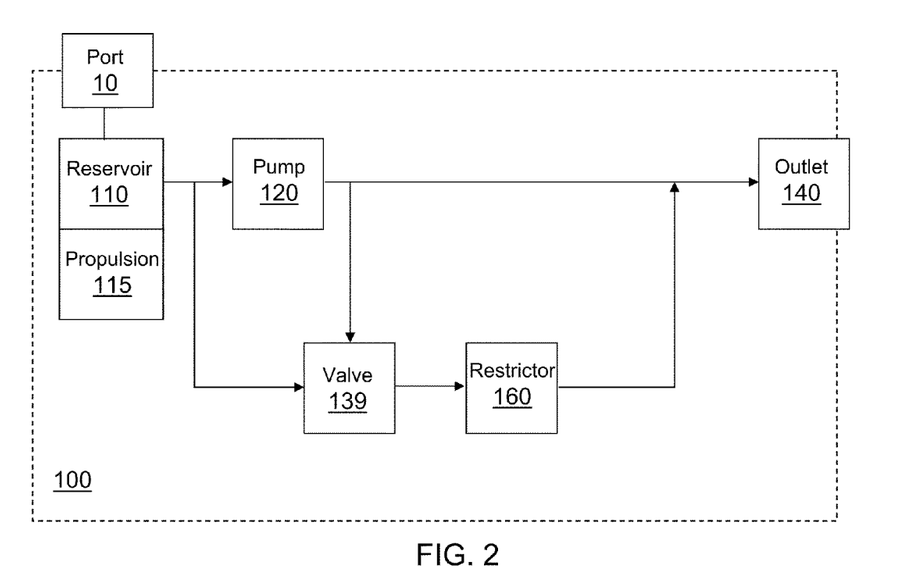

While not shown in FIG. 1, it will be understood that valves may be employed to control whether fluid is delivered from the device 100 via the first or second pathway. For example, and with reference to FIG. 2, a valve 139 is shown disposed upstream of the restrictor 160 in the second pathway. While shown upstream of the restrictor 160, the valve 139, in some embodiments, may be positioned downstream of the restrictor 160. The state of the valve (e.g., whether open or closed) is controllable, e.g. via electrical circuitry, pressure differentials, mechanical forces, or the like. In many embodiments, the controllable valves described herein are MRI-safe valves, such as piezoelectric valves that are stable when exposed to magnetic fields or bistable valves, such as those described in, e.g., U.S. Pat. Nos. 5,820,589 and 6,471,675, which patents are hereby incorporated by reference in their respective entireties to the extent that they do not conflict with the disclosure presented herein.

In numerous embodiments, an implantable infusion device 100 includes a safety valve 150 (see, e.g., FIGS. 3, 4, and 6-8) to control whether fluid flows via the second higher rate flow path. The open-closed state of safety valve 150 is not electrically controlled, and thus the safety valve 150 is not sensitive to magnetic fields and is MRI-safe. Any suitable safety valve, such as those depicted in FIGS. 5A, 5B, and 9, may be employed. In the embodiments depicted in FIGS. 3-9, the safety valve 150 is configured to be closed unless fluid expelled from the pump 120 is diverted to the safety valve, causing the valve to open, activating the higher flow rate pathway.

Figure 3:
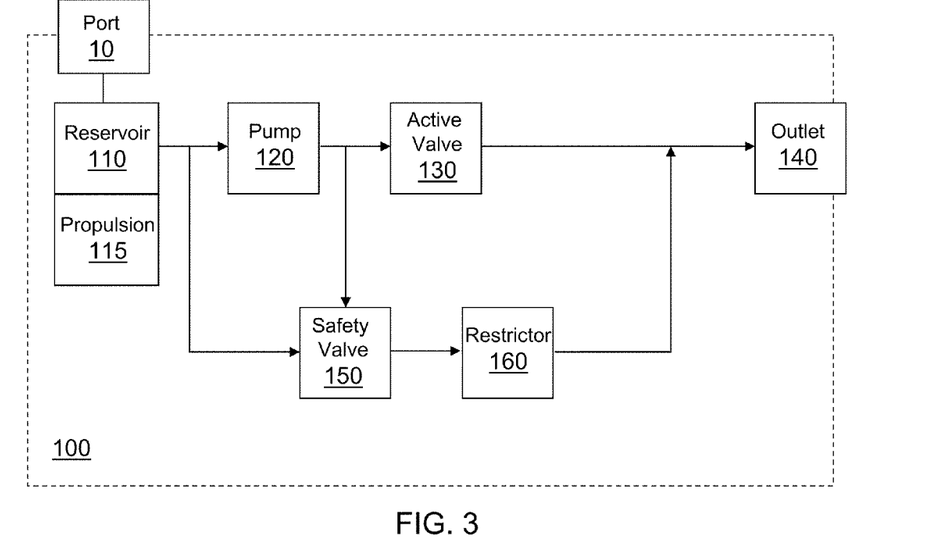

Referring now to FIG. 3, the depicted implantable infusion device includes two flow paths extending from the reservoir 110 to the outlet 140. The first flow path includes a pump 120 downstream of the reservoir 110, and an active valve 130 downstream of the pump 120. The pump 120 is configured to control the rate at which fluid from the reservoir 110 is delivered from the device 100 via the outlet 140. The active valve 130 is configured to be open when it is desired for fluid from the reservoir 110 to be delivered from the device 100 via the first flow path.

Still referring to FIG. 3, the second flow path from the reservoir 110 to the outlet 140 includes a safety valve 150 downstream of the reservoir 110, and a flow restrictor 160 downstream of the safety valve 150. As described above with regard to FIGS. 1-2, the second flow path may be used to deliver fluid from the reservoir 110 at a higher flow rate than via the first flow path. As further described above, the flow rate achievable by the second flow path is determined mainly by the amount of pressure in the reservoir 110 and the design of the flow restrictor 160. As described above with regard to FIGS. 1-2, the reservoir 100 may be operably coupled to a propulsion mechanism 115 to provide positive reservoir pressure.

In cases where flow restrictor 160 is not a variable rate flow restrictor 160, it may be desirable to include an active valve 170 (see FIG. 4) downstream of the restrictor 160. The active valve may be duty-cycled to between open and closed states to control the rate at which fluid exits the device 100 via the second pathway, if desired.

Figure 4:
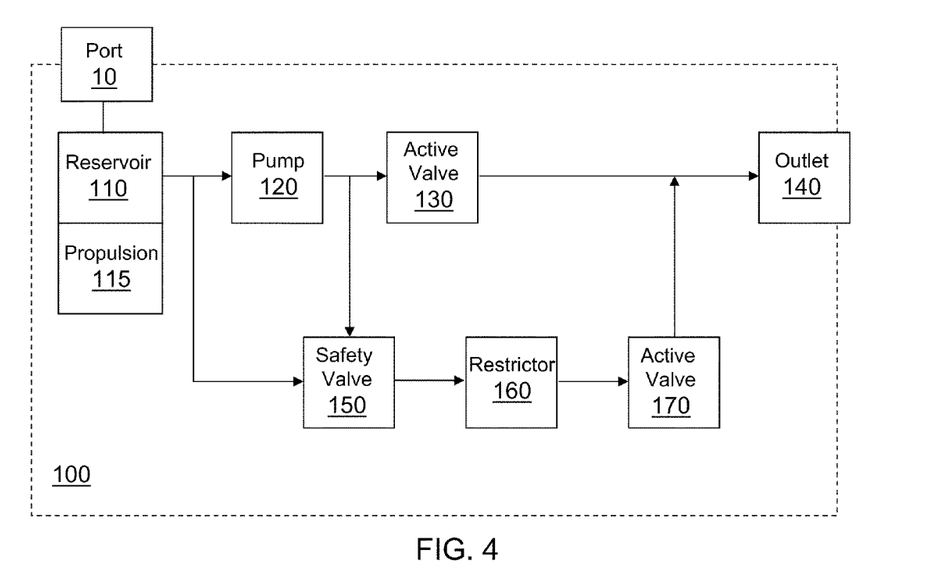

The implantable infusion devices 100 shown in FIGS. 3-4 further include a third flow path from the pump 120 to the safety valve 150. The safety valve 150 is configured to be closed unless the pump 120 is active and the active valve 130 is closed. Thus, unless the pump 120 is active and the active valve 130 is closed, no fluid exits the device 100 via the second pathway. Accordingly, the device 100 is MRI-safe such that if active valve 130 or active valve 170, if present, is inadvertently opened during an MRI procedure, no fluid exits the device 100.

Figure 5A:
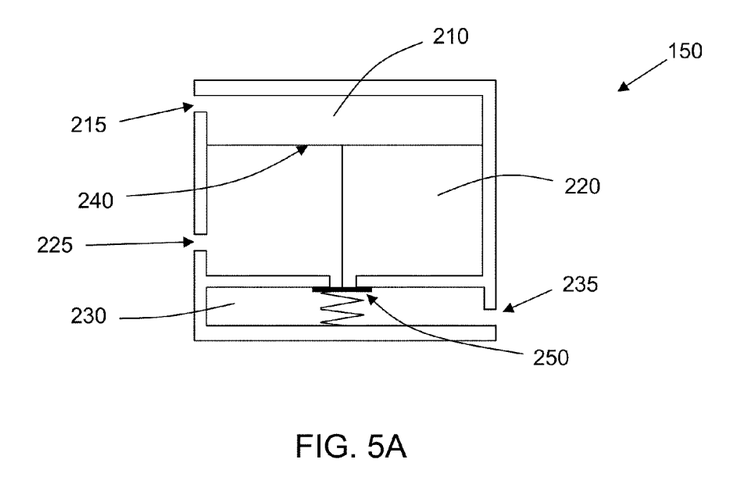
FIGS. 5A-B are schematic diagrams of an embodiment of a safety valve in closed (FIG. 5A) and open (FIG. 5B) states.
Figure 5B:
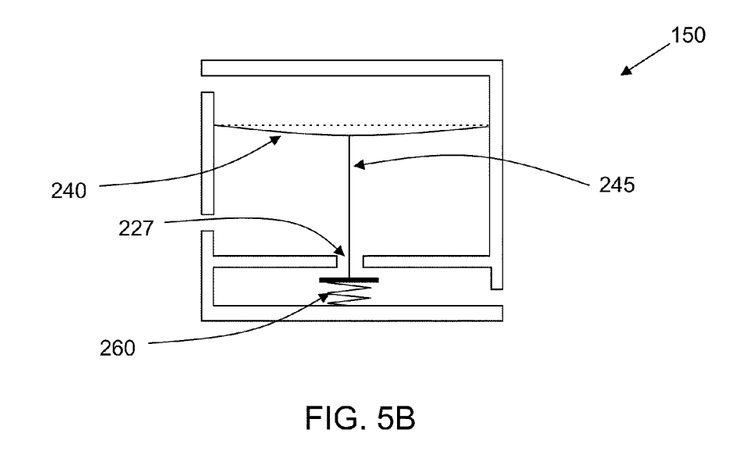

Any suitable safety valve 150 configured to prevent fluid from flowing from the reservoir 110 the restrictor 160 unless the pump 120 is activated and active valve 130 is closed may be employed. For example, and with reference to FIGS. 5A-B, an embodiment of a suitable safety valve 150 is shown. In FIG. 5A, the safety valve 150 is closed. In FIG. 5B, the safety valve 150 is shown as open. In the depicted embodiment, the safety valve 150 includes a first chamber 210 in communication with the pump via opening 215, which forms part of the third flow path, and a second chamber 220 in communication with the reservoir via opening 225, which forms part of the second flow path. A diaphragm 240 sealingly divides the first chamber 210 from the second chamber 220. The safety valve 150 further includes a third chamber 230 in communication with the flow restrictor via opening 235, which forms part of the second flow path. A sealing member 250 is operably coupled to the diaphragm 240 via a rod 245 in the depicted embodiment.

When the pump 120 is on and the active valve 130 (see, e.g., FIGS. 3-4) is closed, fluid is pumped into the first chamber 210 causing pressure to increase and diaphragm 240 to deflect (compare FIG. 5A to FIG. 5B). As the diaphragm 240 deflects due to increased pressure in the first chamber 210, the sealing member 250 moves to allow fluid to flow from the second chamber 220 to the third chamber 230 via opening 227, allowing fluid to flow from the reservoir 110 to the outlet 140 via the second flow path. When active valve 130 is opened, fluid from the pump 150 preferentially flows to outlet 140 rather than into the safety valve 150, and the pressure in first chamber 210 of the safety valve decreases relative to pressure in the second chamber 230 and the diaphragm deflects back to original position (compare FIG. 5A to FIG. 5B), causing sealing member 250 to sealingly engage opening 227 to prevent fluid flow from the second chamber 220 to the third chamber 230. As shown in FIGS. 5A-B, a biasing element 260, such as a spring, may bias the sealing member 260 in the closed position (FIG. 5A). Increased pressure in the first chamber 210 due to pumping fluid into the chamber 210 creates sufficient force and deflection of the diaphragm 240 to overcome the biasing force of the biasing element 260 to allow movement of the sealing member 260 and permit fluid flow from the second 220 to the third 230 chamber.

Components of the device 100 that may come into contact with a fluid therapeutic composition to be delivered via the device are preferably compatible with the composition and therapeutic agent such that the components of the device are not adversely affected by the composition, and the composition and therapeutic agent are not adversely affected by the components of the device. Such materials are known and commonly used in commercially available implantable infusion devices, and include (i) polymers such as silicones and fluorpolymers. (ii) metals such as titanium, stainless steel, and nitinol, and (iii) corrosion resistant alloys such as MP35N. By way of example, the diaphragm 240 may be formed of a suitable material that is impervious to the fluid delivered by the device, such as nitinol, elastomeric polymers, such as fluoropolymers, or a thin metal foil formed from, for example, titanium. The rod 245 may be formed of any suitable material, such as stainless steel, titanium, or the like. Any suitable sealing member 350, such as an O-ring on a plate, may be employed. Biasing element 260 may be formed from any suitable material, such as a metallic material or resilient polymeric material. The housing of the safety valve may be formed of any suitable material, such as a metal or corrosion resistant alloy.

It will be understood that the safety valve 150 depicted in FIGS. 5A-B is but one embodiment of a safety valve that may be employed with devices in accordance with the teachings presented herein and that other safety valves configurations, where the safety valve is configured to be closed unless the pump is active and the active valve in the first flow path is closed, may be employed.

Figure 6:
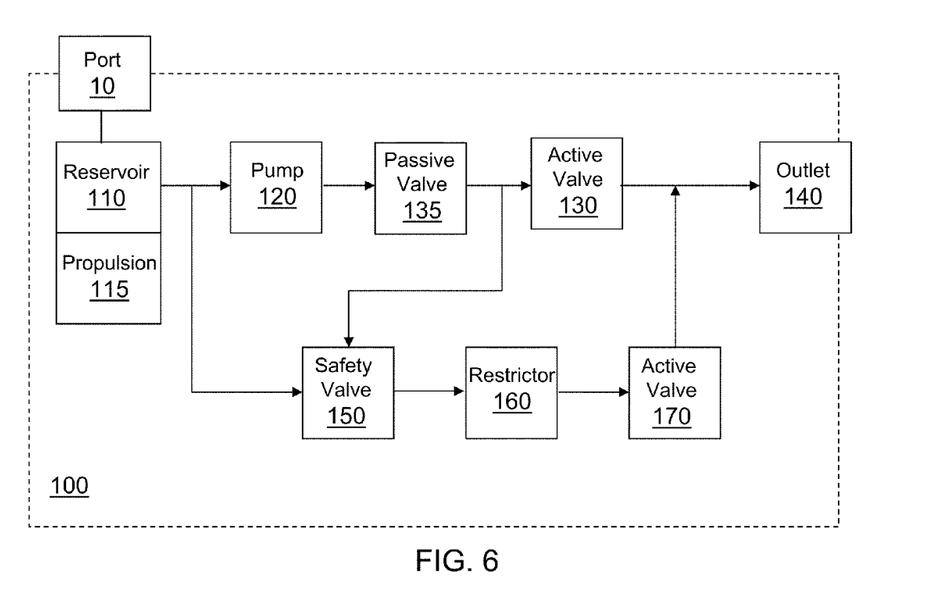
FIGS. 6-8 are schematic block diagrams showing some components of embodiments of implantable infusion devices.

Referring now to FIG. 6, an implantable infusion device 100 may include a passive valve 135 having a cracking pressure greater than the reservoir 110 pressure. The passive valve 135 is depicted as being downstream of the pump 120, but may be upstream of the pump 120 in some embodiments. The passive valve 135 is upstream of active valve 130 and upstream of the safety valve 150. As the cracking pressure of the passive valve 135 is greater than the pressure in the reservoir 110, the passive valve 135 is configured to prevent fluid from flowing to the safety valve 150 and active valve 130 when the pump is inactive or off. In situations where the pump 120 is not capable of holding back or preventing fluid from flowing past the pump 120 from the positive pressure reservoir 110 when the pump is off or deactivated, the passive valve 135 can provide MRI-safety. In the absence of the passive valve 135 in such situations, inadvertent opening of active valve 130 or closing of active valve 130 and opening of active valve 170, if present, may result in inadvertent delivery of fluid via either the first or second fluid path. When the pump 120 is active (e.g., in an non-MRI environment), the pump 120 may pump fluid at a pressure capable of overcoming the cracking pressure of the passive valve 135 to allow fluid to flow via the first (past active valve 130) or third (to safety valve 150) fluid pathways.

However, it will be understood that in many cases, pumps such as peristaltic and piston pumps are configured to prevent fluid flow through the pump when the pump is inactive. When such pumps 120 are employed, passive valve 135 may optionally be employed.

Figure 7:
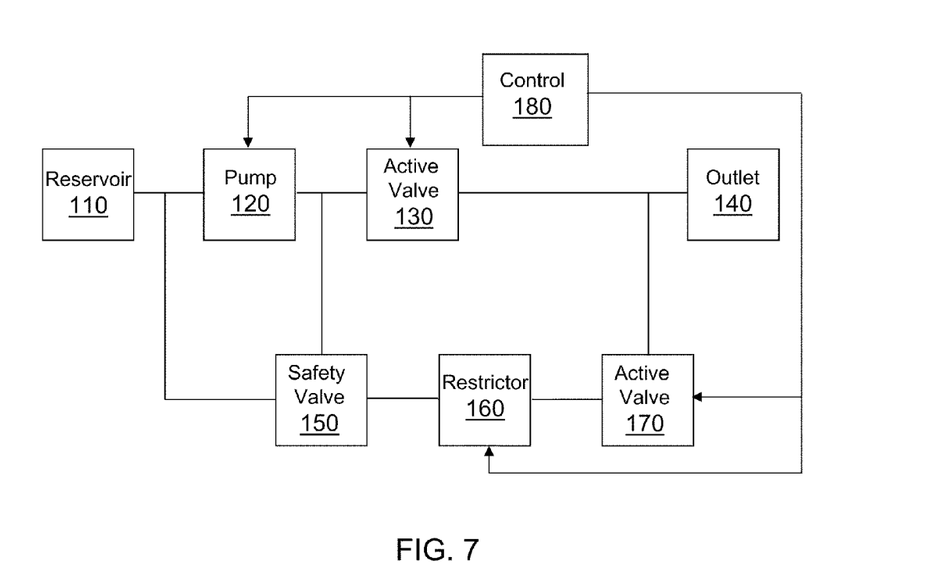

Referring now to FIG. 7, an implantable infusion device as described herein may include a control electronics 180 configured to control the pump 120, active valve 130, and active valve 170 or flow restrictor 160. For example, to activate the second fluid pathway, control electronics may instruct active valve 130 to close and pump 120 to deliver fluid at a rate sufficient to cause the safety valve 150 to open. To fine tune the rate that the fluid is delivered via the second pathway, control electronics 180 may instruct the active valve 170 to cycle between open and closed states.

The control electronics 180 may be provided in any suitable form and may, for example, include memory and a controller. The controller may be, e.g., an Application Specific Integrated Circuit (ASIC) state machine, a gate array, or may include a microprocessor. The control electronics 180 may also include components, etc. to operate other features not depicted in the exemplary system such as flow or pressure sensors, alarms, etc.

The control electronics 180 may further include telemetry components configured to receive or send information from the device implanted in a patient. Telemetry may be used to, e.g., allow programming of the infusion rate, infusion times, etc. Telemetry may further be used to provide information from the infusion device such as, e.g., the amount of fluid in the reservoir, etc. Such information may be used to determine whether the reservoir requires refilling, etc.

While not shown, it will be understood that the implantable infusion device includes a power supply, such as a battery, capacitor, or the like. The power supply may be operably coupled to supply power to the pump mechanism 120, control electronics 180, active valves 130, 170, flow restrictor 160 (in some embodiments), and any other components requiring electric power.

Figure 8:
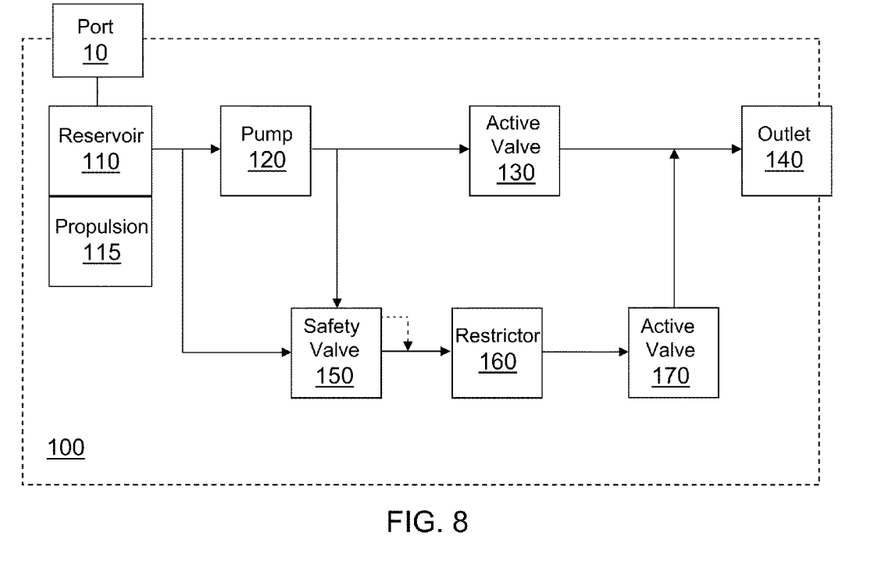

Referring now to FIG. 8, the device 100 may include a fourth fluid pathway (shown in dashed lines) to allow clearing of stagnant fluid from the safety valve 150. The fourth fluid pathway may take any suitable path to accomplish the clearing of stagnant fluid. For example and as depicted, the fourth pathway may run from the safety valve 150 to upstream of the flow restrictor 160. A small amount of fluid may leak from the device via the fourth pathway during normal operation. However, the leakage will be minimal and may be due to a bleed hole incorporated into the safety valve 150.

Figure 9:
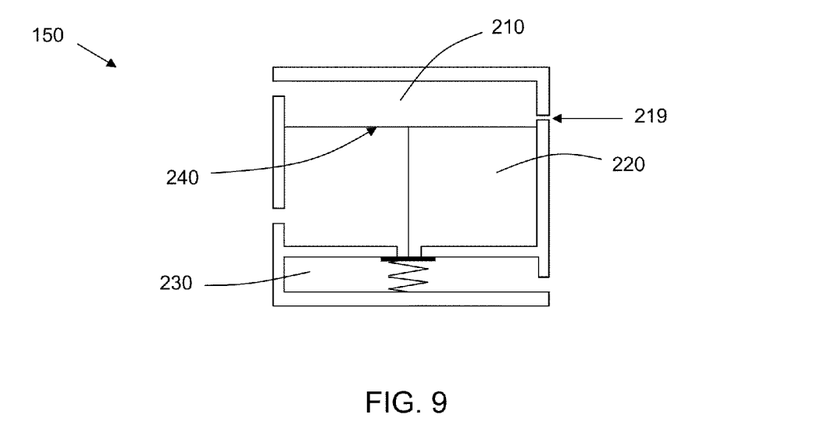
FIG. 9 is a schematic diagram of an embodiment of a safety valve.

For example and with reference to FIG. 9, a safety valve 150 with an optional bleed hole 219 is shown. Bleed hole 219 is in communication with the first chamber 210 of the safety valve 219 and provides for slow leakage of fluid from the first chamber 210 to avoid stagnation of fluid in the chamber 210. The bleed hole 219 is sized and configured to provide sufficient resistance to fluid flow such that sufficient pressure can build up in the first chamber to cause deflection of the diaphragm 240 to open the safety valve (see FIG. 5B). It will be understood that other configurations, such as the use of very high resistance flow restrictors immediately down stream of the safety valve 150 may also be used to provide a leakage pathway for preventing fluid stagnation in the safety valve. Such configurations provide for a small amount of leakage that is unlikely to adversely affect the patient or the therapy.

Figure 10:
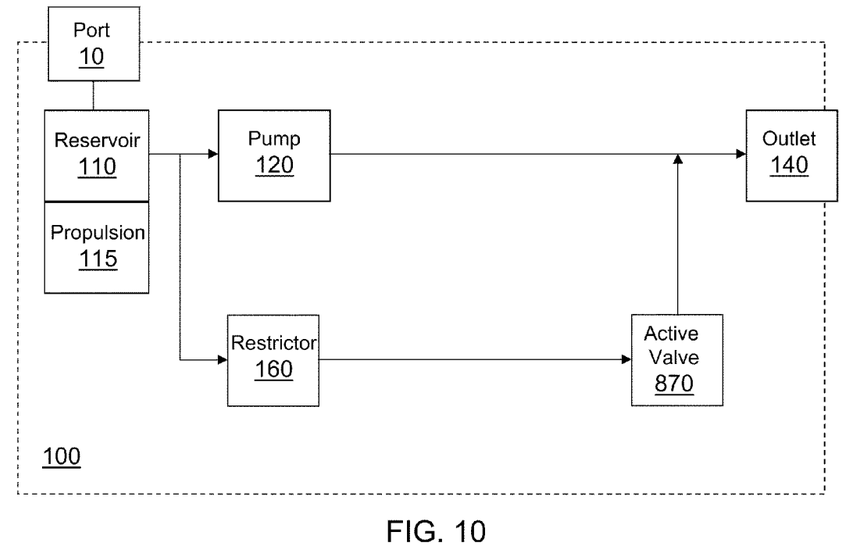
FIGS. 10-11 are schematic block diagrams showing some components of embodiments of implantable infusion devices.

An alternative embodiment of an MRI-safe implantable infusion device 100 having first and second flow paths capable of delivering fluid from a reservoir 110 to an outlet 140 is shown in FIG. 10. In the depicted embodiment, the first flow path includes a positive pressure reservoir 110, a pump 120 downstream of the reservoir 110, and an outlet 140 downstream of the pump 120. The second flow path includes the reservoir 110, a flow restrictor 160 downstream of the reservoir 110, an active valve 870 downstream of the restrictor 160, and the outlet 140 downstream of the active valve 870. It will be understood that the active valve 870 may be disposed in the second flow path upstream of the reservoir (e.g., as depicted for valve 139 in FIG. 2). The active valve 870 in the in the second flow path is an MRI-safe active valve, such as piezoelectric valve that is stable when exposed to magnetic fields or a bistable valve, such as those described in, e.g., U.S. Pat. Nos. 5,820,589 and 6,471,675.

In the device 100 depicted in FIG. 10, the first flow path is configured to deliver fluid from the reservoir 110 to the outlet 140 via the pump 120 at a relatively slower flow rate than from the second flow path. The pump 120 may be any suitable pump, such as those described above with regard to FIGS. 1-4, and 6-8. However, in some embodiments, the pump 120 may be replaced with a fixed or variable rate flow restrictor, such as a restrictor 160 as described above with regard to FIGS. 1, 2 and 4-6; a selectable rate flow restrictor configuration employing a series of valves (e.g., as described in U.S. Pat. Nos. 5,820,589 and 6,471,675); or the like. The second flow path and restrictor 860 may be similar to the second flow path and restrictor 160 described above with regard to FIGS. 1-4, and 6-8.

By using an MRI-safe valve, a safety valve as described above with regard to FIGS. 3-9 may be omitted. Alternatively, MRI-safe-valves may be used in conjunction with such a safety valve.

Figure 11:
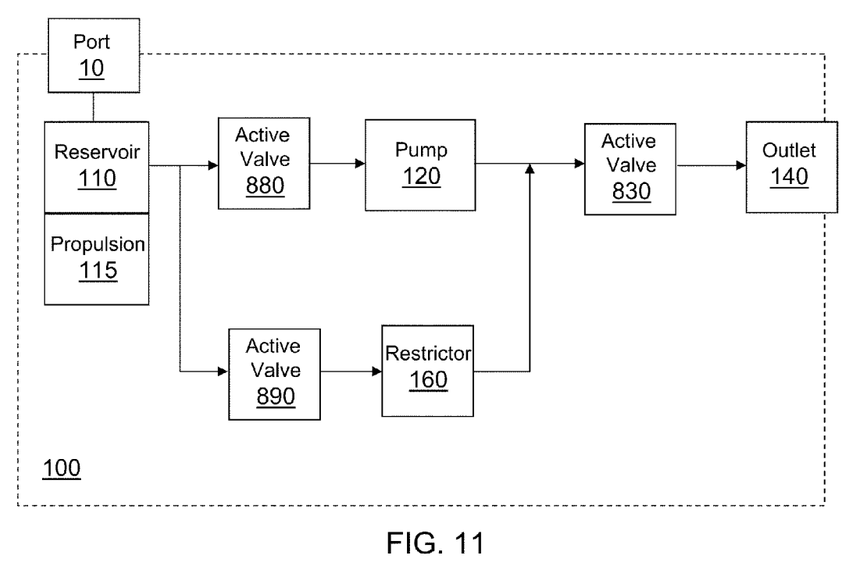

The configuration shown in FIG. 10 is only one example of flow path configurations that may be used to deliver fluid at lower rates and a higher rate via two flow paths using an MRI-safe valve. Any other suitable configuration employing one or more MRI-safe valves may be may be employed. For example, and referring to FIG. 11, an alternative device 100 configuration employing an MRI-safe valve 830 is shown. The reservoir 110, pump 120, restrictor 860, and outlet 140, as well as the first and second flow paths depicted in FIG. 11 may be essentially the same as described above with regard to FIG. 10. In the embodiment depicted in FIG. 11, active valve 880 and active valve 890 may be MRI-safe active valves, but need not be MRI-safe as active valve 830 is an MRI-safe valve and can be configured to prevent fluid from exiting the outlet 140 via ether the first or second flow path. Active valve 880 and active valve 890 may be opened or closed to allow fluid to flow through the first fluid path or the second higher rate flow path.

Figure 12:
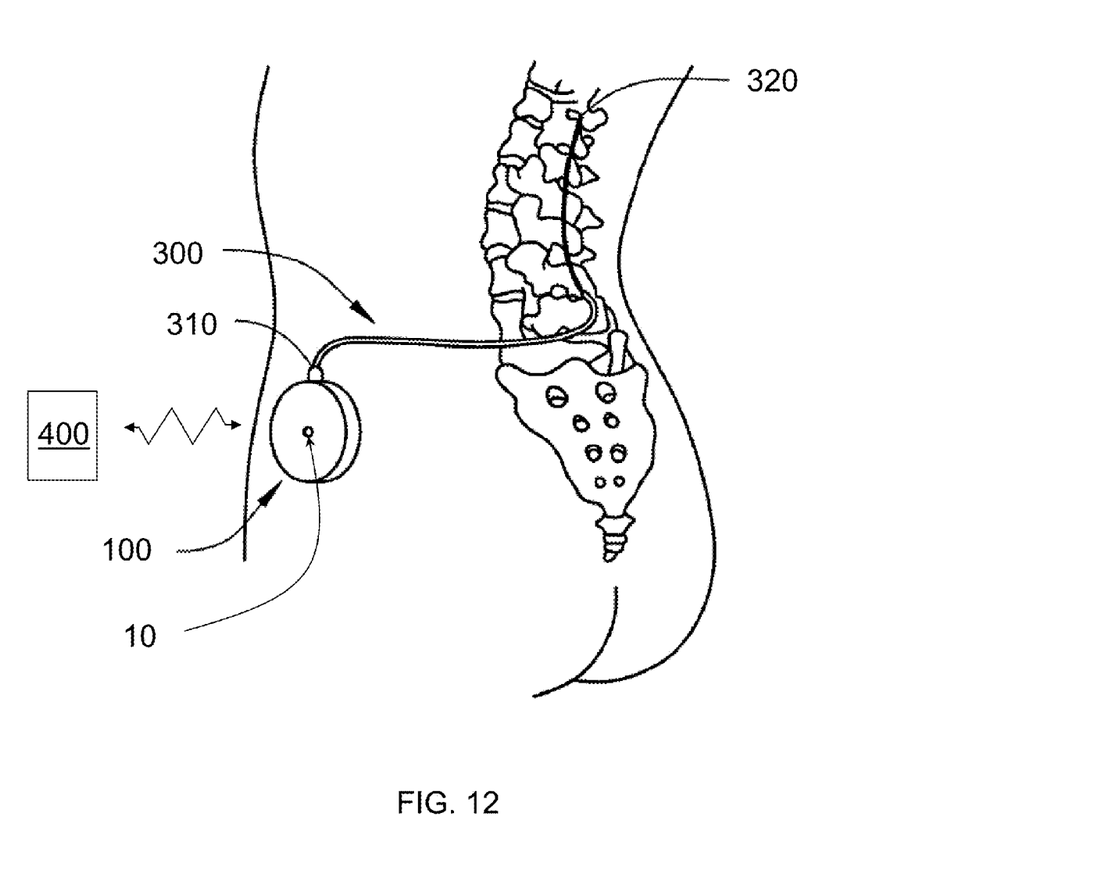
FIG. 12 is a schematic diagram showing an embodiment of an infusion device implanted in a patient.

Although many different infusion systems could be used to practice the methods described herein, an example of one infusion system is shown in FIG. 12. The depicted infusion system includes an infusion device 100 and catheter 300 having a proximal end 310 attached to the infusion device 100 (e.g. in communication with outlet 140 of FIGS. 1-4, 6-8, and 10-11). The pump assembly 100 may be surgically implanted in any suitable location, such as subcutaneously in the pectoral, abdominal or other region of the subject's body. The distal end 320 of the catheter 300 is implanted in a patient such that the distal end 320 is located at a selected internal delivery site in the patient. In the depicted embodiment, the distal end 320 of the catheter 300 is located in the intrathecal space of the patient, but may be positioned at any other suitable and desired location. The infusion device 100 includes a port 10 for accessing a reservoir (not shown) and replenishing fluid in the reservoir. In the depicted embodiment, the system also includes an external device 400, such as a patient or physician programmer, for wireless communication with the implanted device 100.

It will be understood that the various device configurations described herein are but examples of device configurations that may be employed to obtain an infusion device having two different flow paths for delivering fluid at differing rates. It will be further understood that components presented in and discussed with regard to one figure may be readily included in configurations presented in and described with regard to another figure. By way of example, a passive valve 135 as shown in FIG. 6 or control electronics 180 as shown in FIG. 7 may be employed with any other device configuration shown or described herein.

Thus, embodiments of INFUSION DEVICE HAVING WIDE DYNAMIC RANGE FLUID FLOW RATE are disclosed. One skilled in the art will appreciate that the implantable infusion devices having two flow paths can be configured in embodiments other than those disclosed herein. The disclosed embodiments are presented for purposes of illustration and not limitation.

What is claimed is:

1. An implantable infusion device comprising:
   a positive pressure reservoir;
   a pump;
   a flow restrictor;
   an outlet,
   a first fluid flow path from the reservoir to the outlet, wherein the first fluid flow path includes the pump but not the flow restrictor, and wherein the pump is downstream of the reservoir, and the outlet is downstream of the pump;
   a second fluid flow path from the reservoir to the outlet, wherein the second fluid flow path includes the flow restrictor but not the pump, and wherein the flow restrictor is downstream of the reservoir, and the outlet is downstream of the flow restrictor,
   a first controllable valve, wherein the second flow path includes the first controllable valve upstream of the flow restrictor and downstream of the reservoir, wherein the first controllable valve is stable when exposed to a magnetic field;
   a second controllable valve, wherein the first flow path includes the second controllable valve downstream of the pump and upstream of the outlet; and
   third fluid flow path from the pump to the first controllable valve,
   wherein the first controllable valve is configured to prevent flow from the reservoir to the outlet via the second flow path unless the second controllable valve is closed and the pump is activated,
   wherein the first controllable valve comprises a first chamber in communication with the pump via the third flow path, a second chamber in communication with the reservoir via the second flow path, and a diaphragm sealingly dividing the first and second chambers.

2. The device of claim 1, wherein the first controllable valve further comprises a sealing member, a third chamber in communication with the second chamber and the restrictor, wherein the sealing member is operably coupled to the diaphragm and is configured to permit fluid to flow from the second chamber to the third chamber or to fluidly seal the third chamber relative to the second chamber.

3. An implantable infusion device comprising:
   a positive pressure reservoir;
   a pump;
   a flow restrictor;
   an outlet,
   a first fluid flow path from the reservoir to the outlet, wherein the first fluid flow path includes the pump but not the flow restrictor, and wherein the pump is downstream of the reservoir, and the outlet is downstream of the pump;
   a second fluid flow path from the reservoir to the outlet, wherein the second fluid flow path includes the flow restrictor but not the pump, and wherein the flow restrictor is downstream of the reservoir, and the outlet is downstream of the flow restrictor,
   a first controllable valve, wherein the second flow path includes the first controllable valve upstream of the flow restrictor and downstream of the reservoir, wherein the first controllable valve is stable when exposed to a magnetic field;
   a second controllable valve, wherein the first flow path includes the second controllable valve downstream of the pump and upstream of the outlet;
   third fluid flow path from the pump to the first controllable valve,
      wherein the first controllable valve is configured to prevent flow from the reservoir to the outlet via the second flow path unless the second controllable valve is closed and the pump is activated; and
   a fourth leakage flow path configured to provide a leakage flow from the first controllable valve to the flow restrictor.

4. The device of claim 3, wherein the first controllable valve comprises a first chamber in communication with the pump via the third flow path, a second chamber in communication with the reservoir via the second flow path, and a diaphragm sealingly dividing the first and second chambers, wherein the first chamber comprises a bleed hole in communication with the fourth leakage pathway.

5. An implantable infusion device comprising:
   a positive pressure reservoir;
   a pump;
   a flow restrictor;
   an outlet,
   a first fluid flow path from the reservoir to the outlet, wherein the first fluid flow path includes the pump but not the flow restrictor, and wherein the pump is downstream of the reservoir, and the outlet is downstream of the pump;
   a second fluid flow path from the reservoir to the outlet, wherein the second fluid flow path includes the flow restrictor but not the pump, and wherein the flow restrictor is downstream of the reservoir, and the outlet is downstream of the flow restrictor,
   a first controllable valve, wherein the second flow path includes the first controllable valve upstream of the flow restrictor and downstream of the reservoir, wherein the first controllable valve is stable when exposed to a magnetic field;
   a second controllable valve, wherein the first flow path includes the second controllable valve downstream of the pump and upstream of the outlet;
   third fluid flow path from the pump to the first controllable valve,
      wherein the first controllable valve is configured to prevent flow from the reservoir to the outlet via the second flow path unless the second controllable valve is closed and the pump is activated,
      wherein the second controllable valve has an open state and a closed state and wherein the device further comprises control electronics operably coupled to the second controllable valve and the pump, wherein the control electronics are configured to provide instructions to close the second controllable valve and to cause the pump to deliver fluid to the first controllable valve to open the first controllable valve and permit fluid to flow from the reservoir to the outlet via the second flow path; and a third controllable valve in the second fluid pathway, wherein the third controllable valve is downstream of the flow restrictor, and the outlet is downstream of the third controllable valve.

6. The device of claim 5, wherein the control electronics are configured to cause the third controllable valve to cycle between an open state and a closed state to control the rate at which fluid is delivered to the outlet via the second flow path.

* * * * *